(12) United States Patent
Owoc

(10) Patent No.: US 8,435,963 B2
(45) Date of Patent: May 7, 2013

(54) WEIGHT LOSS COMPOSITIONS AND USES THEREOF

(76) Inventor: John H. Owoc, Davie, FL (US)

( * ) Notice: Subject to any disclaimer, the term of this patent is extended or adjusted under 35 U.S.C. 154(b) by 457 days.

(21) Appl. No.: 12/567,323

(22) Filed: Sep. 25, 2009

(65) Prior Publication Data

US 2010/0081626 A1    Apr. 1, 2010

Related U.S. Application Data

(60) Provisional application No. 61/100,422, filed on Sep. 26, 2008.

(51) Int. Cl.
*A61K 31/70* (2006.01)
*A61K 31/7076* (2006.01)
*A61K 31/7052* (2006.01)

(52) U.S. Cl.
USPC ............................ 514/47; 514/46; 514/280

(58) Field of Classification Search .................... 514/47, 514/46, 280
See application file for complete search history.

(56) References Cited

U.S. PATENT DOCUMENTS

2005/0025844 A1*  2/2005  Boldt ............................ 424/734

OTHER PUBLICATIONS

MasSupplement.com, 2008.*
mindandmuscle.com, Aug. 27, 2008.*
Friesen, K., et al., "Benign course after massive ingestion of yohimbine," *J. Emerg. Med.*, 1993, pp. 287-288, vol. 11, No. 3.
Galitzky, J., et al., "Alpha 2-antagonist compounds and lipid mobilization: evidence for a lipid mobilizing effect of oral yohimbine in healthy male volunteers," *Eur. J. Clin. Invest.*, Apr. 19, 1988, pp. 587-594, vol. 18, No. 6.
Grasing, K., et al., "Effects of Yohimbine on Autonomic Measures are Determined by Individual Values for Area Under the Concentration-Time Curve," *J. Clin. Pharmacol.*, 1996, pp. 814-822, vol. 36.
Le Corre, P., et al., "Biopharmaceutics and metabolism of yohimbine in humans," *Eur. J. Pharm. Sci.*, Feb. 3, 1999, pp. 79-84, vol. 9, No. 1.

* cited by examiner

*Primary Examiner* — Shaojia Anna Jiang
*Assistant Examiner* — Michael C Henry
(74) *Attorney, Agent, or Firm* — Saliwanchik, Lloyd & Eisenschenk

(57) ABSTRACT

This invention provides unique and advantageous formulations and methods for weight loss.

4 Claims, No Drawings

WEIGHT LOSS COMPOSITIONS AND USES THEREOF

CROSS-REFERENCE TO A RELATED APPLICATION

This application claims the benefit of U.S. provisional application Ser. No. 61/100,422, filed Sep. 26, 2008, which is incorporated herein by reference in its entirety.

FIELD OF THE INVENTION

The present invention is in the field of dietary supplements, and uses thereof, for promoting good health through weight loss and/or maintenance of proper weight.

BACKGROUND OF INVENTION

Increased weight in individuals, including obesity, has become an epidemic health issue around the world. Obese and overweight individuals develop, at an increased rate, diseases such as cardiovascular disease, diabetes, sleep apnea, osteoarthritis, and cancer. Consequently, obese and overweight individuals now exhibit a reduced overall life expectancy. Haslam D W and James W P, "Obesity" *Lancet* 2005;366(9492):1197-209. Unfortunately, these weight-related issues are now also being observed more commonly in children.

Treatment of obese or overweight individuals can include improved diet and physical exercise. However, efforts to diet and exercise are not successful for everyone. Sedentary lifestyles, ready availability of poor dietary choices, genetic risk factors, and stress all can make it difficult to lose unwanted weight. Medication has offered avenues to lose weight by, for example, reducing the absorption of fat that has been ingested in the diet. However, drug treatments may only result in modest weight reduction, can include deleterious side effects, and may not have a beneficial effect on the long-term issues related to increased weight e.g., diabetes, cardiovascular disease, etc.

Some individuals opt for surgery to lose weight by, for example, reducing the size of the stomach or reducing the length of the bowels. However, complications from surgery are frequent and behavior modification is needed to enhance the likelihood of a successful outcome. Encinosa W E, Bernard D M, Chen C C, and Steiner C A, "Healthcare utilization and outcomes after bariatric surgery," *Medical Care* 2006;44(8):706-12.

In addition, those individuals who do not fall into the overweight or obese classification, characterized as a body mass index (BMI)<25, World Health Organization Technical Report Series 894: *"Obesity: Preventing and Managing the Global Epidemic"* Geneva: World Health Organization (2000), can also benefit from reduced body fat. These so called normal weight, or even under weight, individuals may desire improved physical performance and appearance resulting from decreased weight. In this category of individuals, the treatments for weight reduction differ from the obese and overweight individuals and primarily rely on physical exercise and diet rather than medical or surgical treatments.

Nutritional supplements are one method of weight reduction used by individuals regardless of weight classification. Numerous types of supplements exist affecting different factors related to weight loss. Certain supplements are aimed at, for example, appetite suppression, decreased nutrient absorption, or increased metabolism. However, these supplements often possess potential problems and harmful side effects of their own. Supplements intended for reducing appetite may not work as intended because the neural basis of appetite is not fully understood. Supplements for blocking absorption of dietary fats may cause oily stools, stomach pain, and flatulence. Metabolic stimulant supplements can carry a risk of high blood pressure, faster heart rate, palpitations, closed-angle glaucoma, drug addiction, restlessness, agitation, and insomnia.

There is thus a great need for a weight loss composition that facilitates fat burning and/or weight loss, while decreasing the side effects known to be associated with other weight loss methods and compositions.

BRIEF SUMMARY

The subject invention provides stable aqueous compositions of at least one biologically-active fat loss agent. In one preferred embodiment the compositions of the subject invention comprise at least one agent that stimulates a receptor of the beta adrenergic receptor family and at least one agent that inhibits a receptor of the alpha adrenergic receptor family.

In a preferred embodiment, the compositions of the subject invention comprise:
  a) Yohimbine;
  b) 11-hydroxy yohimbine;
  c) alpha-yohimbine;
  d) methyl synephrine;
  e) methyl PEA isomers;
  f) methyl hordenine; and
  g) methyl tetradecylthioacetic acid.

Advantageously, these compositions are stable across a wide range of pHs and temperatures. These formulations may have, for example, a pH of from about 3 to about 7 or more, and are stable at temperatures between 4° C. (or less) and 40° C. (or more). Advantageously, across this wide range of conditions, the concentration of bioactive species in these compositions does not decrease appreciably over periods of 40 or even 60 days or more.

The compositions of the subject invention may further comprise one or more additional materials selected from, for example, flavoring agents, colorants, viscosity modifiers, preservatives, fragrances, amino acids and their salts, vitamins, minerals, essential fatty acids, enzymes, co-enzymes, mono-glycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants.

The subject invention further provides methods for preparing and using these compositions. The subject invention may be used as a dry mixture blended in water, juice, milk, or any other drinkable liquid. The blended composition may then be delivered enterally as a beverage. The subject invention may be produced as a ready-mixed beverage for consumption.

In accordance with the invention, the subject composition and methods utilize a combination of elements that increase weight loss in individuals in an advantageous and synergistic manner. As such, the synergistic effects of the subject composition and methods offer increased efficacy. In addition, the advantageous elements of the subject composition reduce the harmful side effects common to other methods of weight loss treatment.

DETAILED DISCLOSURE

The subject invention is particularly useful in the field of weight loss compositions and methods. While the subject invention is exemplified with respect to use for weight reduction, other modifications apparent to a person with skill in the art and having benefit of the subject disclosure are contemplated to be within the scope of the present invention.

The present invention provides unique solutions to address the problem of weight loss. The materials and methods of the subject invention address not just single molecules, messengers, or receptors, but instead act on multiple points in the fat-burning pathway. Additionally, the combination of compounds disclosed herein results in a synergistic effect that achieves weight loss more quickly and on a more permanent basis than previous treatments.

The subject invention provides stable aqueous compositions of at least one biologically-active fat loss agent. In a specific embodiment, the compositions of the subject invention comprise:
  a) yohimbine;
  b) 11-hydroxy yohimbine;
  c) alpha-yohimbine;
  d) methyl synephrine;
  e) methyl PEA isomers;
  f) methyl hordenine; and
  g) methyl tetradecylthioacetic acid.

In one preferred embodiment the compositions of the subject invention comprise at least one agent that stimulates a receptor of the beta adrenergic receptor family and at least one agent that inhibits a receptor of the alpha adrenergic receptor family.

Reference herein to "comprise" should be understood to include "consisting essentially of" and "consisting of" "Consisting essentially of" means that the composition does not contain additional components that materially affect the composition's ability to effect weight loss.

In the body, adrenergic receptors closely mediate the disposition of fat stores. These receptors bind epinephrine and norepinephrine with varying specificity and potency to manage numerous bodily functions. As related to weight loss and thermogenesis, the body runs a tightly regulated mechanism where stimulation of beta adrenergic receptors triggers the release of fatty acids from adipose cells and stimulation of alpha adrenergic receptors blocks the breakdown and release of fatty acids from the cells. This balance provides an opportune focus to stimulate or antagonize the receptors in one way or another for the ultimate goal of weight loss.

Certain agents are focused on stimulation of the beta adrenergic receptor family in order to increase the breakdown and release of fatty acids, otherwise known as lipolysis, in adipose tissues. Ephedrine is one example of a beta receptor agonist that was previously used in weight loss compositions. Ephedrine is a strong, non-selective activator of lipolytic and thermogenic activity mediated by the beta-2 and beta-3 receptors. However, the non-selectivity of ephedrine results in overstimulation of the central nervous system through the beta-1 and beta-2 adrenergic receptors. The overstimulation of beta-1 and beta-2 receptors generates unwanted or dangerous side effects such as hypertension, tachycardia, increased heart rate, nausea, or insomnia. Consequently, focus on specific stimulators of beta-3 adrenergic receptors provides a potent avenue for lipolysis and thermogenesis while decreasing the occurrence of harmful side effects. One such agonist of the beta-3 receptors is synephrine. Synephrine is specific for the beta-3 receptors and, thus, does not exhibit the side effects of the chemically related ephedrine.

On the other side of the balance, agents may be directed at inhibition of the alpha adrenergic receptor family. The alpha adrenergic receptor antagonists block the signaling pathway that negatively regulates lipolysis in adipose cells. Thus, stimulation of the beta receptors will be favored and lipolysis will result. Yohimbine (IUPAC: 17α-hydroxy-yohimban-16α-carboxylic acid methyl ester) is one example of an extremely potent naturally-occurring alpha-2 receptor antagonist. In addition, yohimbine also strongly stimulates the synaptic release of norepinephrine, an endogenous beta receptor-agonist that in turn triggers lipolysis. As such, yohimbine serves a dual purpose, both blocking alpha-2 receptor activation and increasing the level of norepinephrine available to fat cells. Galitzky J. Taouis M, Berlan M. Rivière D, Garrigues M, and Lafontan M, "Alpha 2-antagonist compounds and lipid mobilization: evidence for a lipid mobilizing effect of oral yohimbine in healthy male volunteers." *Eur. J. Clin. Invest.* 1998;18:587-94.

Yohimbine blocks the inhibitory mechanisms against lipolysis and strengthens the response toward lipolysis. Of note, yohimbine does not possess the harmful side effects found with beta agonists such as ephedrine as larger doses are tolerated and do not lead to problematic heart rate or blood pressure. Friesen K, Palatnick W, and Tenenbein M, "Benign course after massive ingestion of yohimbine." *J. Emerg. Med.* 1993;11:287-288; Grasing K, Sturgill M G, Rosen R C, Trout J R, Thomas T J, Kulkarni G D, Maines P, and Seibold J R. "Effects of Yohimbine on Autonomic Measures are Determined by Individual Values for Area Under the Concentration-Time Curve," *J. Clin. Pharmacol.* 1996;36:814-822.

Yohimbine is also available in alternative forms other than the pure yohimbine HCl form commonly used in supplements. Alpha-yohimbine and 11-hydroxy yohimbine are also shown to act as antagonists of the alpha-adrenergic receptors and stimulate the release of norepinephrine. 11-Hydroxy yohimbine, a natural metabolite of yohimbine, also exhibits an increased half-life from 2.5 hours of yohimbine HCl to 8-11 hours for the 11-hydroxy metabolite. Le Corre P, Dollo G, Chevanne F, and Le Verge R, "Biopharmaceutics and metabolism of yohimbine in humans." *Eur. J. Pharm. Sci.* 1991;9(1):79-84.

Yohimbine, alpha-yohimbine, and 11-hydroxy yohimbine are included in this invention for the synergistic effects as an alpha-2 receptor antagonist. In addition, the yohimbine combination also strongly stimulates the synaptic release of norepinephrine in an improved manner over the administration of yohimbine alone.

Methyl synephrine can be used according to the subject invention specifically for the increase in fat burning potential. The methyl-modified synephrine works as an alpha-1 and beta-3 adrenergic agonist to stimulate lipolysis. Further, methyl synephrine works without acting upon the central nervous system as does its chemically related compound ephedrine.

Preferred compositions of the subject invention comprise one or more yohimbine compounds (e.g. yohimbine, 11-hydroxy yohimbine, and alpha-yohimbine) as an inhibitor of the alpha adrenergic receptor and also comprise synephrine as a stimulator of the beta adrenergic receptor. The composition may also optionally contain one or more compounds selected from methyl PEA isomers; methyl hordenine; and methyl tetradecylthioacetic acid.

Methyl PEA isomers, such as R-beta methylphenylethylamine, R-beta methoxyphenylethylamine, and n-methyl beta methylphenylethylamine, can be used to increase fat loss and reduce cravings. The methyl PEA isomers exhibit increased passage through the blood brain barrier and slower rates of metabolism. The R-beta modification has stimulant effects and slows down metabolism by monoamine oxidases.

Methyl hordenine can be used according to the subject invention as a more potent monoamine oxidase (MAO)

inhibitor. The methyl-modified hordenine MAO-inhibitory function results in slower metabolization of the methyl PEA isomers thus increased activity of the methyl PEA isomers. In addition, hordenine stimulates further release of norepinephrine.

Methyl tetradecylthioacetic acid (MTTA) can be used to increase the number of mitochondria in cells to in turn increase the fat burning potential of each cell. MTTA decreases the storage of fat and improves insulin sensitivity. Further, the methyl-modified acid demonstrates an unexpected increase in apoptosis of adipose cells and decrease in the proliferation of adipose cells.

In a specific embodiment of the invention, the weight loss composition comprises yohimbine, alpha-yohimbine, 11-hydroxy yohimbine, methyl synephrine, R-beta methylphenylethylamine, n-methyl beta methylphenylethylamine, methyl hordenine, and methyl tetradecylthioacetic acid.

In a further embodiment of the invention, the weight loss composition further comprises caffeine and/or cAMP.

In a specific embodiment, the subject invention provides aqueous compositions suitable for oral administration to mammals including, without limitation, humans.

In a specific embodiment, the subject invention may be used as a dry mixture blended in water, juice, milk, or any other drinkable liquid. The blended composition may then be delivered enterally as a beverage.

A composition as provided herein may be administered chronically. As used herein, "chronically" has its normal meaning, which generally means repeated ingestion over a period of several days, several weeks or even several months or more. Acute administration may also be utilized.

The compositions of the subject invention can be used in a variety of advantageous methods. For example, these compositions can be used in a method in which the compositions of the subject invention may further comprise one or more additional materials selected from the group consisting of flavoring agents, colorants, viscosity modifiers, preservatives, fragrances, amino acids and their salts, vitamins, minerals, essential fatty acids, enzymes, co-enzymes, monoglycerides, di-glycerides, tri-glyceride ester oils emulsifiers, hydrolyzed proteins, whey protein, stabilizers, flow modifiers, viscosity improvers, chelating agents, anti-oxidants, anti-microbials, benzoates, alcohols, esters of para-hydroxybenzoic acid, propionates, preservatives and surfactants. Advantageously, these compositions are stable across a wide range of pHs and temperatures.

The compositions of the subject invention can be formulated for a variety of modes of administration. These formulations include, but are not limited to, compositions for oral administration, aqueous injectable formulations, injectable emulsion compositions, gel formulations, cream formulations, transdermal systems, transdermal patch systems, liquid buccal sublingual solutions, oral solid compositions, lipid delivery formulations, rapid and sustained release formulations, and oral liquid composition with protein.

Following are examples that illustrate procedures for practicing the subject invention. These examples are provided for the purpose of illustration only and should not be construed as limiting. Thus, any and all variations that become evident as a result of the teachings herein or from the following examples are contemplated to be within the scope of the present invention.

EXAMPLE 1

Thermogenic Effect Achieved with a Composition of the Subject Invention

This study examined the acute effect of a weight loss supplement of the subject invention on resting oxygen uptake ($VO_2$), respiratory quotient (RQ), caloric expenditure (kcal), heart rate (HR), and blood pressure (BP) in healthy and physically active individuals.

Methods

Ten subjects (5 male, 5 female; 20.2±1.2 y; 172.2±8.9 cm; 71.5±17.2 kg; 17.3±2.6% body fat) underwent two testing sessions administered in a randomized and double-blind fashion. During each session, subjects reported to the Human Performance Laboratory after at least 3-h post-absorptive state and were provided either 3 capsules of the weight loss supplement (S), commercially marketed as MELTDOWN® or 3 capsules of a placebo (P). MELTDOWN® comprises yohimbine, 11-hydroxy yohimbine, alpha-yohimbine, methyl synephrine, R-beta-methylphenylethylamine, hordenine, and α-MTTA.

Subjects then rested in a semi-recumbent position for three hours. $VO_2$ and HR were determined every 5 min during the first 30 min and every 10 min during the next 150 min. BP was determined every 15 min during the first 30 min and every 30 min thereafter. The profile of mood states was determined every 30 minutes. Area under the curve (AUC) analysis was computed for $VO_2$, whereas a 3 hour average and an average for each/hour was calculated for RQ, kcal from carbohydrate, kcal from fat, total kcal, HR and BP.

Results

AUC analysis revealed a significant 28.9% difference in $VO_2$ between S and P for the three hour study period. In addition, a significant difference in energy expenditure was also seen between S (1.28±0.33 kcal·min$^{-1}$) and P (1.00±0.32 kcal·min$^{-1}$) during the entire three hour study. A trend (p=0.06) towards a greater utilization of stored fat as an energy source was also demonstrated (0.78±0.23 kcal·min$^{-1}$ and 0.50±0.38 kcal·min$^{-1}$ in S and P. respectively). Significant elevations in heart rate were seen during hour 3 of the study, and significantly higher systolic blood pressures were observed between S (118.0±7.3 mmHg) and P (111.4±8.2 mmHg). No significant differences were seen in diastolic blood pressure at any time point. Analysis of mood states indicated a significant increase in tension during the supplement period compared to placebo.

Conclusion

A significant increase in energy expenditure was achieved in young, healthy individuals following an acute ingestion of a weight loss supplement of the subject invention.

EXAMPLE 2

Increase in Energy Expenditure and Fat Oxidation

This study evaluated the effects of a thermogenic supplement of the subject invention, VPX MELTDOWN®, on energy expenditure, fat oxidation, and hemodynamics before and after maximal treadmill exercise.

Methods

In a double-blind, placebo-controlled, cross-over design, participants underwent two testing sessions after consuming either the VPX MELTDOWN® or placebo supplement. Healthy male participants (n=12) aged 18-35 rested for one hour while energy expenditure (EE), respiratory exchange ratio (RER), heart rate (HR), and blood pressure (BP) were assessed in a fasted state. Subsequently, participants orally ingested either supplement or placebo. Immediately following supplement administration, participants rested for another hour while EE, RER, HP, and BP were recorded. Thereafter, participants performed a maximal exercise test on a treadmill and then endured another hour of EE, RER, HR, and BP measurement.

Results

VPX MELTDOWN®, increased REE significantly more than placebo at 45 minutes (2,079±373 vs. 1,847±340 kcal/day; p=0.003) and 60 minutes (2,153±403 vs. 1877±314 kcal/day; p=0.025) post-ingestion. Furthermore, REE 60 minutes post-exercise (two to three hours following supplement administration) was higher in the MELTDOWN® group (2,179±386 vs. 1,913±400; p=0.1440). Moreover, over the course of the three hour evaluation period, area under the curve assessment demonstrated that EE was significantly increased with VPX MELTDOWN® compared to placebo (area: 9,925±1,331 vs. 8,951±2,961; p=0.043) while RER was significantly less than placebo (area: 5.55±0.61 vs. 5.89±0.44; p=0.002) following ingestion. HR and BP were not significantly affected prior to exercise with either supplement (p>0.05) and the exercise-induced increases observed in HR and BP that decreased into recovery were not different between supplements (p>0.05).

Conclusion

These data suggest that VPX MELTDOWN® enhances EE and fat oxidation more than placebo for several hours after ingestion in fully rested and post-exercise states without any adverse hemodynamic responses.

EXAMPLE 3

Specific Composition

In one embodiment of the subject invention, MELTDOWN® has the following composition:

| Serving Size (4 fl oz [120 mL]) | |
|---|---|
| | Amount per Serving |
| Sodium | 10 mg |
| Proprietary Blend | 152 mg |
| Caffeine Anhydrous | 115 mg |
| R-beta-Methylphenylethylamine HCl | |
| N-Methyl-beta Phenylethylamine | |
| Methyl-Synephrine HCl | |
| Yohimbe (*Coryanthe yohimbe*) (bark) [std. to 11-hydroxy yohimbine] | |
| A-MTTA (alpha Methyl Tetradecylthioacetic Acid) | |
| 3'5'-cAMP (3'5'-Cyclic Adenosine Monophosphate) | |
| Barley (*Hordeum vulgare*) (bud)[std. to horderine HCl] | |
| Yohimbe [*Caryanthe yohimbe*) (back)[std. to alpha Yohimbine HCl] | |

Other Ingredients: highly purified water, citric acid, natural & artificial flavors, Sucralean ® brand sucralose, malic acid, sodium benzoate (preserves freshness), potassium citrate monohydrate and calcium disodium EDTA.

All patents, patent applications, provisional applications, and publications referred to or cited herein are incorporated by reference in their entirety, including all figures and tables, to the extent they are not inconsistent with the explicit teachings of this specification.

It should be understood that any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is submitted that it is within the purview of one skilled in the art to effect such feature, structure, or characteristic in connection with other embodiments.

It should be understood that the examples and embodiments described herein are for illustrative purposes only and that various modifications or changes in light thereof will be suggested to persons skilled in the art and are to be included within the spirit and purview of this application.

I claim:

1. A composition for inducing weight loss wherein said composition consists essentially of:
   a) yohimbine;
   b) 11-hydroxy yohimbine;
   c) alpha-yohimbine;
   d) methyl synephrine;
   e) R-beta methylphenylethylamine;
   f) n-methyl beta methylphenylethylamine and/or n-methyl beta phenylethylamine;
   g) methyl hordenine; and
   h) methyl tetradecylthioacetic acid.

2. A composition for inducing weight loss wherein said composition consists of:
   a) yohimbine;
   b) 11-hydroxy yohimbine;
   c) alpha-yohimbine;
   d) methyl synephrine;
   e) R-beta methylphenylethylamine;
   f) n-methyl beta methylphenylethylamine and/or n-methyl beta phenylethylamine;
   g) methyl hordenine;
   h) methyl tetradecylthioacetic acid; and, optionally,
   one or more further ingredients selected from the group consisting of caffeine, cAMP, water, flavoring agents, colorants, viscosity modifiers, preservatives, fragrances, vitamins, minerals, enzymes, co-enzymes, emulsifiers, stabilizers, flow modifiers, viscosity improvers, chelating agents, anti-oxidants, anti-microbials, alcohols, propionates, and surfactants.

3. A method of inducing weight loss in a mammal, comprising administering to said mammal a weight loss inducing amount of the composition of claim 1.

4. A composition for inducing weight loss wherein said composition consists essentially of:
   a) yohimbine;
   b) 11-hydroxy yohimbine;
   c) alpha-yohimbine;
   d) methyl synephrine;
   e) R-beta methylphenylethylamine;
   f) n-methyl beta methylphenylethylamine and/or n-methyl beta phenylethylamine;
   g) methyl hordenine;
   h) methyl tetradecylthioacetic acid; and
   one or more ingredients selected from the group consisting of caffeine, cAMP, water, flavoring agents, colorants, viscosity modifiers, preservatives, fragrances, vitamins, minerals, enzymes, co-enzymes, emulsifiers, stabilizers, flow modifiers, viscosity improvers, chelating agents, anti-oxidants, anti-microbials, alcohols, propionates, and surfactants.

* * * * *